United States Patent [19]

Krapcho et al.

[11] 4,267,354

[45] May 12, 1981

[54] SUBSTITUTED AMIDES HAVING ANTIINFLAMMATORY ACTIVITY AND INTERMEDIATES

[75] Inventors: John Krapcho, Somerset; Chester F. Turk, Kendall Park, both of N.J.

[73] Assignee: E. R. Squibb & Sons, Inc., Princeton, N.J.

[21] Appl. No.: 118,173

[22] Filed: Feb. 4, 1980

Related U.S. Application Data

[62] Division of Ser. No. 33,299, Apr. 25, 1979, Pat. No. 4,216,335, which is a division of Ser. No. 897,476, Apr. 18, 1978, Pat. No. 4,166,072, which is a division of Ser. No. 773,561, Mar. 2, 1977, Pat. No. 4,098,789.

[51] Int. Cl.$^3$ .................. C07C 101/30; C07C 103/26
[52] U.S. Cl. ............................. 560/39; 260/326.41; 544/162; 544/168; 544/399; 544/400; 546/233; 546/235; 564/165; 424/248.54; 424/248.55; 424/267; 424/309; 424/324
[58] Field of Search .................. 260/326.41; 544/168, 544/399, 400, 162; 546/233, 235; 560/39; 564/165

[56] References Cited

U.S. PATENT DOCUMENTS

| | | | |
|---|---|---|---|
| 2,774,766 | 12/1956 | Goldberg et al. | 546/232 |
| 3,103,516 | 9/1963 | Schmitt et al. | 546/233 |
| 3,167,556 | 1/1965 | Krapcho | 260/558 P X |
| 3,192,213 | 6/1965 | Krapcho | 260/558 P X |
| 3,201,401 | 8/1965 | Krapcho | 260/558 D X |
| 3,378,586 | 4/1968 | Krapcho | 260/558 P |
| 3,515,753 | 6/1970 | Bernstein et al. | 260/558 P |
| 3,551,492 | 12/1970 | Mizzoni | 260/570.7 R |
| 3,632,779 | 1/1972 | Marshall | 424/330 |
| 4,064,125 | 12/1977 | Krapcho | 544/306 |
| 4,098,789 | 7/1978 | Krapcho et al. | 544/299 |

OTHER PUBLICATIONS

Millonig et al., Chem. Absts., 81, 163,333(x), 1974.
Nakamura et al., Chem. Absts., 82, 14677(f), 1975.
Geller et al., Chem. Absts., 83, 141972(u), 1975.

Primary Examiner—G. T. Breitenstein
Attorney, Agent, or Firm—Lawrence S. Levinson; Donald J. Barrack

[57] ABSTRACT

Compounds having the formula

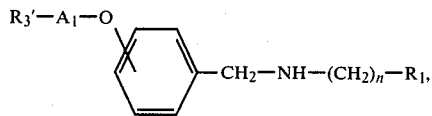

wherein $R_1$ is alkoxycarbonyl, amido, alkylamido, or dialkylamido; $R'_3$ is alkylbenzylamino, dialkylamino, 1-pyrrolidinyl, 1-piperidinyl, 4-morpholinyl, or 4-alkyl-1-piperazinyl; $A_1$ is an alkylene group having 2 to 5 carbon atoms; and n is 1, 2 or 3; are intermediates useful in the preparation of substituted amides having antiinflammatory activity.

3 Claims, No Drawings

SUBSTITUTED AMIDES HAVING ANTIINFLAMMATORY ACTIVITY AND INTERMEDIATES

This is a division of application Ser. No. 33,299, filed Apr. 25, 1979, now U.S. Pat. No. 4,216,335, which is a division of application Ser. No. 897,476, filed Apr. 18, 1978, now U.S. Pat. No. 4,166,072, issued Aug. 28, 1979, which is a division of application Ser. No. 773,561, filed Mar. 2, 1977, now U.S. Pat. No. 4,098,789, issued July 4, 1978.

RELATED APPLICATION

Copending U.S. patent application Ser. No. 736,990, filed Oct. 29, 1976 by John Krapcho, discloses and claims compounds that are related to the compounds of the instant application.

BRIEF DESCRIPTION OF THE INVENTION

Compounds having the formula

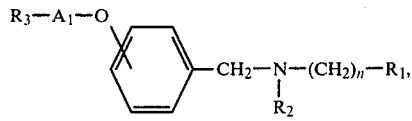

or a pharmaceutically acceptable salt thereof, have useful antiinflammatory activity. In formula I, and throughout the specification, the symbols are as defined below.

$R_1$ is alkoxycarbonyl, amido, alkylamido, or dialkylamido;

$R_2$ is

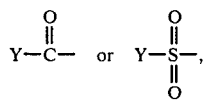

wherein Y is alkyl, cycloalkyl, aryl, arylalkyl, styryl or styryl wherein the phenyl group is substituted with a halogen, alkyl, alkoxy, trifluoromethyl, nitro or amino group;

$R_3$ is alkylamino, dialkylamino or a nitrogen containing heterocyclic group selected from 1-pyrrolidinyl, 1-piperidinyl, 4-morpholinyl, and 4-alkyl-1-piperazinyl;

$A_1$ is an alkylene group having 2 to 5 carbon atoms; and n is 1, 2 or 3.

The terms "alkyl" and "alkoxy", as used throughout the specification, whether by themselves or as part of larger groups, refer to groups having 1 to 6 carbon atoms.

The term "aryl", as used throughout the specification, whether by itself or as part of a larger group, refers to phenyl or phenyl substituted with a halogen, alkyl, alkoxy, trifluoromethyl, nitro, or amino group.

The term "halogen", as used throughout the specification, refers to fluorine, chlorine, bromine and iodine; chlorine and bromine are preferred.

The term "cycloalkyl", as used throughout the specification, refers to cycloalkyl groups having 3 to 7 carbon atoms.

The term "alkylene", as used throughout the specification, refers to a straight or branched chain, divalent, saturated hydrocarbon group.

DETAILED DESCRIPTION OF THE INVENTION

The compounds of this invention can be prepared using as starting materials a benzaldehyde having the formula

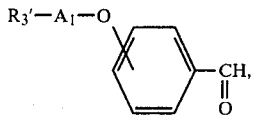

wherein $R'_3$ is alkylbenzylamino, dialkylamino or a nitrogen containing heterocyclic group, and a primary amine having the formula $$H_2N-(CH_2)_n-R_1 \quad \text{III}$$

Reaction of a benzaldehyde of formula II with an amine of formula III yields the corresponding Schiff base having the formula

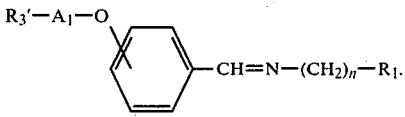

The reaction can be run in an organic solvent, e.g., ethanol or an aromatic hydrocarbon such as toluene, and is usually run without the addition of heat.

Reduction of a compound of formula IV, using chemical or catalytic means, yields the corresponding intermediate having the formula

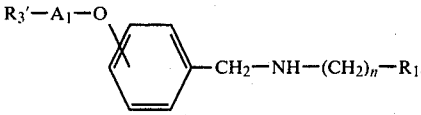

The reaction can be run using gaseous hydrogen in the presence of a catalyst such as Raney nickel or palladium. Preferably, the reaction will be run using a chemical reducing agent such as sodium borohydride.

The Schiff bases of formula IV and the compounds of formula V are novel compounds useful in the preparation of the antiinflammatory compounds of formula I; as such, they constitute a part of this invention.

The products of formula I, wherein $R_3$ is dialkylamino or a nitrogen containing heterocyclic group, can be prepared by reacting a compound of formula V, wherein $R'_3$ is dialkylamino or a nitrogen containing heterocyclic group, with an acid or sulfonyl halide, preferably an acid or sulfonyl chloride, having the formula $$R_2-Cl \quad \text{VI}$$

or, when $R_2$ is

an acid anhydride having the formula

   VII can also be used. The reaction can be run in an organic solvent, e.g., a halogenated hydrocarbon such as chloroform.

The products of formula I, wherein $R_3$ is alkylamino, can be prepared by first reacting a compound of formula V, wherein $R'_3$ is alkylbenzylamino, with a compound of formula VI or VII as described above to yield an intermediate having the formula

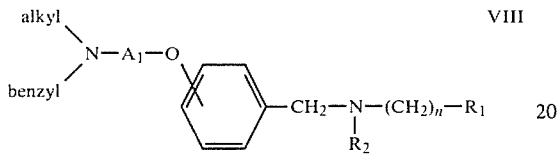   VIII

Debenzylation of a compound of formula VIII using the well-known catalytic hydrogenation procedure yields the corresponding product of formula I.

Those products of formula I wherein the $R_2$ group contains an amino substituent are preferably prepared by reduction of the corresponding nitro compound.

The pharmaceutically acceptable salts of the compounds of formula I are readily prepared using procedures well known in the art. Acid addition salts are specifically contemplated. Exemplary salts are the hydrohalides, sulfate, nitrate, phosphate, oxalate, tartrate, maleate, citrate, benzenesulfonate, and others.

The compounds of formula I, and the pharmaceutically acceptable salts thereof, can be used for the treatment of inflammation in mammalian species such as mice, dogs, cats, monkeys, etc. Joint tenderness and stiffness (in conditions such as rheumatoid arthritis) are relieved by the compounds of this invention. Formulation of the compounds can be carried out according to accepted pharmaceutical practice in oral dosage forms such as tablets, capsules, elixirs or powders, or in injectable form in a sterile vehicle. The compounds of this invention can be administered in amounts of about 0.1 to 2.0 grams per 70 kilograms of animal body weight per day, preferably about 0.1 to 1.0 gram per 70 kilograms of animal body weight per day.

The following examples are specific embodiments of this invention.

EXAMPLE 1

[[[2-[3-(Dimethylamino)propoxy]phenyl]methyl](1-oxo-3-phenyl-2-propenyl)amino]acetic acid, ethyl ester, oxamate salt (1:2)

(A)

[[[2-[3-(Dimethylamino)propoxy]phenyl]methylene]amino]acetic acid, ethyl ester

A stirred solution of 15 g of 2-(3-dimethylaminopropoxy)benzaldehyde and 10.2 g of glycine, ethyl ester, hydrochloride in 300 ml of ethanol is treated with 4.8 g of 85% potassium hydroxide and stirring continued for 3 hours at room temperature. Potassium chloride is filtered off, washed with ethanol, and the solvent is removed on a rotary evaporator (water bath temperature, 30°–35° C.). The residue is dissolved in ether, filtered, and the evaporation repeated to give 20.9 g of an oil. The material is stored in the cold.

(B)

[[[2-[3-(Dimethylamino)propoxy]phenyl]methyl]amino]acetic acid, ethyl ester

A stirred solution of the above Schiff base (20.8 g) in 250 ml of ethanol is cooled to 20° C. and treated portionwise with 8.3 g of sodium borohydride. After stirring at room temperature for 4 hours (temperature kept at less than 30° C.), the bulk of ethanol is removed on a rotary evaporator and the cooled residue is shaken with 50 ml of water and 100 ml of ether. The layers are separated, the aqueous phase extracted with additional ether (four 100 ml portions), the combined ether layers washed with water (30 ml), dried, and the solvent evaporated to give 17.3 g of an oily residue. Distillation yields 12.1 g of an oil; boiling point 154°–160° C./0.2–0.3 mm of Hg.

(C)

[[[2-[3-(Dimethylamino)propoxy]phenyl]methyl](1-oxo-3-phenyl-2-propenyl)amino]acetic acid, ethyl ester The above amine (17.2 g) and 10.0 g of cinnamoyl chloride are reacted in 240 ml of chloroform by first cooling a stirred solution of cinnamoyl chloride in chloroform to 15° C. and then treating the solution dropwise with a solution of the amine in chloroform. A cold water bath is used to maintain the temperature at 10°–15° C. After stirring for about an hour at room temperature, the solution is heated at reflux for an additional hour. The solution is cooled and the chloroform evaporated.

The semi-solid residue is converted to the oily base by treatment with potassium carbonate in water, and extraction into ether to yield 22.7 g of base. The base is chromatographed on 500 g of Woelm basic alumina (Activity III), and eluted with a total of 2 liters of chloroform to yield 15.3 g of base.

(D)

[[[2-[3-(Dimethylamino)propoxy]phenyl]methyl](1-oxo-3-phenyl-2-propenyl)amino]acetic acid, ethyl ester, oxamate salt (1:2)

The above base (15.3 g) and 6.4 g of oxamic acid are dissolved in 100 ml of warm methanol, filtered, and diluted to cloudiness with ether. On scratching and rubbing, the crystalline salt gradually separates. More ether is added and after cooling for about 16 hours, the material is filtered, washed with ether, and dried in vacuo, yielding 19.1 g of material; melting point 103°–105° C. (sintering at 100° C.). Following crystallization from methanol-ether, the product weighs 16.5 g; melting point 105°–107° C. (sintering at 102° C.).

EXAMPLE 2

N-(2-Amino-2-oxoethyl)-N-[[2-[3-(dimethylamino)-propoxy]phenyl]methyl]-3-phenyl-2-propenamide, hydrochloride (1:1)

(A)

2-[[[2-[3-(Dimethylamino)propoxy]phenyl]methylene]amino]acetamide

Fifteen grams of 2-(3-dimethylaminopropoxy)benzaldehyde and 8.1 g of glycinamide, hydrochloride are reacted in 300 ml of ethanol in the presence of 4.8 g of 85% potassium hydroxide as described in Example 1 to give 20 g of a crude semi-solid product. The crude product is triturated with 100 ml of isopropyl ether and cooled to yield 17.9 g of solid; melting point 71°–73° C. (sintering at 60° C.).

(B)
2-[[[2-[3-(Dimethylamino)propoxy]phenyl]methyl]amino]acetamide

The above Schiff base (17.3 g) is reduced with 7.6 g of sodium borohydride in 140 ml of methanol as described in Example 1 to give 15.7 g of a viscous oil. The corresponding dioxalate salt has a melting point of 167°–169° C.

(C)
N-[2-Amino-2-oxoethyl)-N-[[2-[3-(dimethylamino)propoxy]phenyl]methyl]-3-phenyl-2-propenamide, hydrochloride The above amine (7.4 g) and 5.0 g of cinnamoyl chloride are reacted in 80 ml of chloroform as described in Example 1 (addition carried out at 10°–15° C.). The colorless solid product which separates during the reflux period is cooled, filtered, washed with chloroform and with ether, and dried in vacuo to yield 5.7 g of material; melting point 190°–192° C. The chloroform-ether liquor is evaporated to give 6.8 g of sticky foamy residue which when shaken with water and ether, basified with potassium carbonate, separated, and further extracted with ether, yields 2.4 g of a viscous oil. The latter gives an additional 0.9 g of the title hydrochloride salt (melting point 190°–192° C.) when treated in 20 ml of acetonitrile with an equivalent of alcoholic hydrogen chloride. The two fractions are combined and 6.3 g of material is crystallized from 400 ml of acetonitrile. The final yield of product is 5.4 g; melting point 192°–194° C.

EXAMPLE 3
[(4-Chlorobenzoyl)[[2-[3-(dimethylamino)propoxy]phenyl]methyl]amino]acetic acid, ethyl ester, barbiturate salt (1:2)

Twenty-one grams of [[[2-[3-(dimethylamino)propoxy]phenyl]methyl]amino]acetic acid, ethyl ester (see Example 1B) and 13 g of p-chlorobenzoyl chloride are reacted in 300 ml of chloroform as described in Example 1 to give 25.5 g of a viscous oil. The latter is chromatographed on 500 g of Woelm basic alumina (Activity III). The desired base (13.9 g) is eluted with a total of 1 liter of chloroform.

The base (13.5 g) and 8.0 g of barbituric acid are dissolved in 500 ml of boiling methanol, filtered while hot, and the solvent removed on a rotary evaporator. The solid residue is rubbed under ether (the evaporation is repeated), triturated with 200 ml of boiling acetonitrile, and cooled for about 16 hours to give 16.8 g of material; melting point 186°–190° C. (sintering at 160° C.). Following recrystallization from 1.5 l of acetonitrile containing 35 ml of dimethylformamide, the solid weighs 14.5 g; melting point 190°–193° C. (sintering at 166° C.).

EXAMPLE 4
N-(2-Amino-2-oxoethyl)-4-chloro-N-[[2-[3-(dimethylamino)propoxy]phenyl]methyl]benzamide, hydrochloride (1:1)

Ten grams of 2-[[[2-[3-(Dimethylamino)propoxy]phenyl]methyl]amino]acetamide (see Example 2B) and 7.1 g of p-chlorobenzoyl chloride are reacted in 110 ml of chloroform as described in Example 1. The finely-divided, solid product separates at the end of the addition; crude yield, after standing for about 16 hours at room temperature, 10.2 g; melting point 195°–197° C. dec, sintering at 175° C. Work-up of the mother liquor does not yield any additional product. Following crystallization (of 9.7 g) from 50 ml of warm methanol-100 ml of ether, the material weighs 6.3 g; melting point 198°–200° C., dec, sintering at 175° C.

EXAMPLES 5–22

Following the procedure of Example 1 (without the final salt formation), but substituting the compound listed in column I for 2-(3-dimethylaminopropoxy)benzaldehyde, the compound listed in column II for glycine, ethyl ester, hydrochloride, and the compound listed in column III for cinnamoyl chloride, yields the compound listed in column IV.

|   | Column I | Column II | Column III | Column IV |
| --- | --- | --- | --- | --- |
| 5 | 2-(2-diisopropylaminoethoxy)-benzaldehyde | glycine, methyl ester, hydrochloride | phenylacetyl chloride | [[[2-[2-(diisopropylamino)ethoxy]phenyl]methyl](1-oxo-2-phenylethyl)amino]acetic acid, methyl ester |
| 6 | 2-[4-(1-pyrrolidinyl)butoxy]-benzaldehyde | glycine, ethyl ester, hydrochloride | propionyl chloride | [[[2-[4-(1-pyrrolidinyl)butoxy]phenyl]methyl](1-oxopropyl)amino]acetic acid, ethyl ester |
| 7 | 3-[2-(1-piperidinyl)ethoxy]-benzaldehyde | glycine, propyl ester, hydrochloride | benzoyl chloride | [[[3-[2-(1-piperidinyl)ethoxy]phenyl]methyl](benzoyl)amino]acetic acid, propyl ester |
| 8 | 2-[5-(4-morpholinyl)pentoxy]-benzaldehyde | glycine, butyl ester, hydrochloride | 4-bromobenzoyl chloride | [[[2-[5-(4-morpholinyl)pentoxy]phenyl]methyl](4-bromobenzoyl)amino]acetic acid, butyl ester |
| 9 | 4-[2-(4-ethyl-1-piperazinyl)-ethoxy]benzaldehyde | glycine, pentyl ester, hydrochloride | 3-trifluoromethyl-benzoyl chloride | [[[4-[2-(4-ethyl-1-piperazinyl)ethoxy]phenyl]methyl](3-trifluoromethylbenzoyl)amino]acetic acid, pentyl ester |
| 10 | 2-[3-(4-methyl-1-piperazinyl)-propoxy]benzaldehyde | glycine, hexyl ester, hydrochloride | 2-methylbenzoyl chloride | [[[2-[3-(4-methyl-1-piperazinyl)propoxy]phenyl]methyl](2-methylbenzoyl)amino]acetic acid, hexyl |
| 11 | 2-(2-dimethylaminoethoxy)- | glycine, ethyl ester, | 2-methoxybenzoyl | [[[2-[2-(dimethylamino)- |

| | Column I | Column II | Column III | Column IV |
|---|---|---|---|---|
| | benzaldehyde | hydrochloride | chloride | ethoxy]phenyl]methyl](2-methoxybenzoyl)amino]-acetic acid, ethyl ester |
| 12 | 2-(3-diisopropylamino-propoxy)benzaldehyde | glycine, ethyl ester, hydrochloride | cyclohexanoyl chloride | [[[2-[3-(diisopropyl-amino)propoxy]phenyl]-methyl](cyclohexanoyl)-amino]acetic acid, ethyl ester |
| 13 | 2-[4-(1-pyrrolidinyl)butoxy]-benzaldehyde | glycinamide, hydro-chloride | cycloheptanoyl chloride | N-(2-amino-2-oxoethyl)-N-[[2-[4-(1-pyrrolidinyl)-butoxy]phenyl]methyl]-cycloheptanamide |
| 14 | 3-[2-(1-piperidinyl)ethoxy]-benzaldehyde | 2-amino-N,N-diethylacetamide, hydrochloride | phenylacetyl chloride | N-[2-(diethylamino)-2-oxoethyl]-N-[[3-[2-(1-piperidinyl)ethoxy]-phenyl]methyl]phenyl-acetamide |
| 15 | 2-[3-(4-morpholinyl)propoxy]-benzaldehyde | 2-amino-N-methylacetamide, hydrochloride | 3-(4-chlorophenyl)-2-propenoyl chloride | N-[2-(methylamino)-2-oxoethyl]-N-[[2-[3-(4-morpholinyl)propoxy]-phenyl]methyl]-3-(4-chlorophenyl)-2-propen-amide |
| 16 | 2-[3-(4-ethyl-1-piperazinyl)-propoxy]benzaldehyde | glycinamide, hydro-chloride | 3-(2-methylphenyl)-2-propenoyl chloride | N-(2-amino-2-oxoethyl)-N-[[2-[3-(4-ethyl-1-piperazinyl)propoxy]phenyl]-methyl]-3-(2-methylphenyl)-2-propenamide |
| 17 | 3-[2-(4-methyl-1-piperazinyl)-ethoxy]benzaldehyde | glycinamide, hydro-chloride | 3-(2-methoxyphenyl)-2-propenoyl chloride | N-(2-amino-2-oxoethyl)-N-[[3-[2-(4-methyl-1-piperazinyl)ethoxy]-phenyl]methyl]-3-(2-methoxyphenyl)-2-propen-amide |
| 18 | 3-(2-dimethylaminoethoxy)-benzaldehyde | glycinamide, hydro-chloride | 3-(3-trifluoromethyl-phenyl)-2-propenoyl chloride | N-(2-amino-2-oxoethyl)-N-[[3-[2-(dimethylamino)-ethoxy]phenyl]methyl]-3-(3-trifluoromethyl-phenyl)-2-propenamide |
| 19 | 4-(2-dimethylaminoethoxy)-benzaldehyde | glycinamide, hydro-chloride | propionyl chloride | N-(2-amino-2-oxoethyl)-N-[[4-[2-(dimethylamino)-ethoxy]phenyl]methyl]-propionamide |
| 20 | 2-(2-dimethylaminoethoxy)-benzaldehyde | 4-aminobutyramide, hydrochloride | benzenesulfonyl chloride | N-(4-amino-4-oxobutyl)-N-[[2-[2-(dimethylamino)-ethoxy]phenyl]methyl]ben-zenesulfonamide |
| 21 | 3-(2-dimethylaminoethoxy)-benzaldehyde | 3-aminopropionamide, hydrochloride | methanesulfonyl chloride | N-(3-amino-3-oxopropyl)-N-[[3-[2-(dimethylamino)-ethoxy]phenyl]methyl]-methanesulfonamide |
| 22 | 4-(2-dimethylaminoethoxy)-benzaldehyde | 3-aminopropionic acid, methyl ester, hydro-chloride | propionyl chloride | [[[4-[2-(dimethylamino)-ethoxy]phenyl]methyl]-(1-oxopropyl)amino]pro-pionic acid, methyl ester |

EXAMPLE 23

[[[2-[3-(Methylamino)propoxy]phenyl]methyl](1-oxo-3-phenyl-2-propenyl)amino]acetic acid, ethyl ester, oxamate salt (1:2)

A.

[[[2-[3-(N-Benzyl-N-methylamino)propoxy]phenyl]me-thyl](1-oxo-3-phenyl-2-propenyl)amino]acetic acid, ethyl ester, oxamate salt (1:2)

Following the procedure of Example 1, but substituting 2-[3-(N-benzyl-N-methylamino)propoxy]benzaldehyde for 2-(3-dimethylaminopropoxy)benzaldehyde, yields the title compound.

B.

[[[2-[3-(Methylamino)propoxy]phenyl]methyl](1-oxo-3-phenyl-2-propenyl)amino]acetic acid, ethyl ester, oxamate salt (1:2)

A suspension of 10 parts of material from part A in 100 ml of ethanol is treated with 1 part of 5% palladium on carbon and placed under 3 atmospheres of gaseous hydrogen and shaken until 1 equivalent of hydrogen is consumed. The mixture is filtered to remove the catalyst and the solvent is evaporated under reduced pressure to yield the title compound.

EXAMPLE 24

[[[2-[3-(Dimethylamino)propoxy]phenyl]methyl][1-oxo-3-(4-nitrophenyl)-2-propenyl]amino]acetic acid, ethyl ester, oxamate salt (1:2)

Following the procedure of Example 1, but substituting 3-(4-nitrophenyl)-2-propenoyl chloride for cinnamoyl chloride, yields the title compound.

EXAMPLE 25

[[[2-[3-(Dimethylamino)propoxy]phenyl]methyl][1-oxo-3-(4-aminophenyl)-2-propenyl]amino]acetic acid, ethyl ester, oxamate salt (1:2)

A suspension of 10 parts of [[[2-[3-(dimethylamino)propoxy]phenyl]methyl][1-oxo-3-(4-nitrophenyl)-2-propenyl]amino]acetic acid, ethyl ester, oxamate salt (1:2) in 100 ml of ethanol is treated with 1 part of 5% palladium on carbon and placed under 3 atmospheres of gaseous hydrogen. The mixture is shaken until one equivalent of hydrogen is consumed, filtered and the solvent evaporated under reduced pressure to give the title compound.

What is claimed is:

1. A compound having the formula

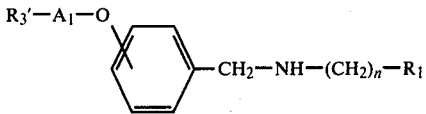

wherein $R_1$ is alkoxycarbonyl, amido, alkylamido or dialkylamido;

$R'_3$ is alkylbenzylamino, dialkylamino, 1-pyrrolidinyl, 1-piperidinyl, 4-morpholinyl, or 4-alkyl-1-piperazinyl;

$A_1$ is an alkylene group having 2 to 5 carbon atoms; and n is 1, 2 or 3.

2. The compound in accordance with claim 1, [[[2-[3-(dimethylamino)propoxy]phenyl]methyl]amino]acetic acid, ethyl ester.

3. The compound in accordance with claim 1, 2-[[[2-[3-(dimethylamino)propoxy]phenyl]methyl]amino]acetamide.

UNITED STATES PATENT AND TRADEMARK OFFICE
CERTIFICATE OF CORRECTION

PATENT NO. : 4,267,354
DATED : May 12, 1981
INVENTOR(S) : John Krapcho, et al.

It is certified that error appears in the above-identified patent and that said Letters Patent are hereby corrected as shown below:

In the table at the bottom of columns 5 and 6, Example 10, Column IV, after the word "hexyl" add --ester--

Signed and Sealed this

Thirteenth Day of October 1981

[SEAL]

Attest:

Attesting Officer

GERALD J. MOSSINGHOFF
Commissioner of Patents and Trademarks